United States Patent [19]

Horneffer

[11] Patent Number: 4,753,637
[45] Date of Patent: Jun. 28, 1988

[54] CATHETER HAVING MEANS FOR CONTROLLING THE INSERTION DEPTH

[75] Inventor: Peter J. Horneffer, Baltimore, Md.

[73] Assignee: The John Hopkins University, Baltimore, Md.

[21] Appl. No.: 886,289

[22] Filed: Jul. 16, 1986

[51] Int. Cl.[4] .................................................. A61M 25/00
[52] U.S. Cl. ..................................... 604/53; 128/344; 604/96; 604/178; 604/280
[58] Field of Search ..................... 128/344, 656–658, 128/399–400; 604/52–53, 4, 95–104, 113, 178, 278, 280–284

[56] References Cited

U.S. PATENT DOCUMENTS

| 724,913 | 4/1903 | Montgomery | 604/278 |
|---|---|---|---|
| 1,497,722 | 6/1924 | Holst-Grubbe | 604/178 |
| 1,852,351 | 4/1932 | Lewis | 604/96 X |
| 3,788,328 | 1/1974 | Alley et al. | 604/178 |
| 4,089,337 | 5/1978 | Kronner | 604/178 X |
| 4,100,923 | 7/1978 | Southern | 604/104 X |
| 4,416,280 | 11/1983 | Carpenter | 604/113 X |
| 4,516,578 | 5/1985 | Shuffield | 604/104 X |
| 4,596,563 | 6/1986 | Pande | 604/280 X |
| 4,610,661 | 9/1986 | Possis et al. | 604/52 |
| 4,648,384 | 3/1987 | Schmukler | 604/101 X |
| 4,689,041 | 8/1987 | Corday et al. | 604/53 |

Primary Examiner—Dalton L. Truluck
Attorney, Agent, or Firm—Cushman, Darby & Cushman

[57] ABSTRACT

A catheter having a tube and a depth control flange to prevent the catheter tube from being over inserted. The preferred embodiment is a retrograde coronary sinus cardioplegia solution administration catheter. A depth control flange is coupled to the tube at a predetermined distance from the catheter tip. The flange is a disc made of soft plastic material which prevents over-insertion of the catheter tip when the flange abuts the wall of the atrium. The catheter tube further includes an inflatable balloon located between the flange and the catheter tip. After insertion into the coronary sinus, the balloon is inflated thus pinching the atrium wall between the flange and the balloon to prevent cardioplegia solution from flowing back from the coronary sinus into the atrium. A semi-rigid introducer tube surrounds a portion of the catheter tube and is axially movable with respect thereto. One end of the introducer tube includes a receptacle in which the flange is stored in a collapsed position. The compact apparatus is inserted into the atrium through a purse string opening in the atrium and then the introducer tube is held steady while the catheter tube is pushed toward the coronary sinus. The flange exits from the receptical and opens like an umbrella and engages the wall of the atrium, thus preventing over-insertion of the catheter in the coronary sinus. The catheter tube includes an air passageway used to inflate the balloon, and a fluid passageway used to provide the cardioplegia solution to the coronary sinus.

17 Claims, 2 Drawing Sheets

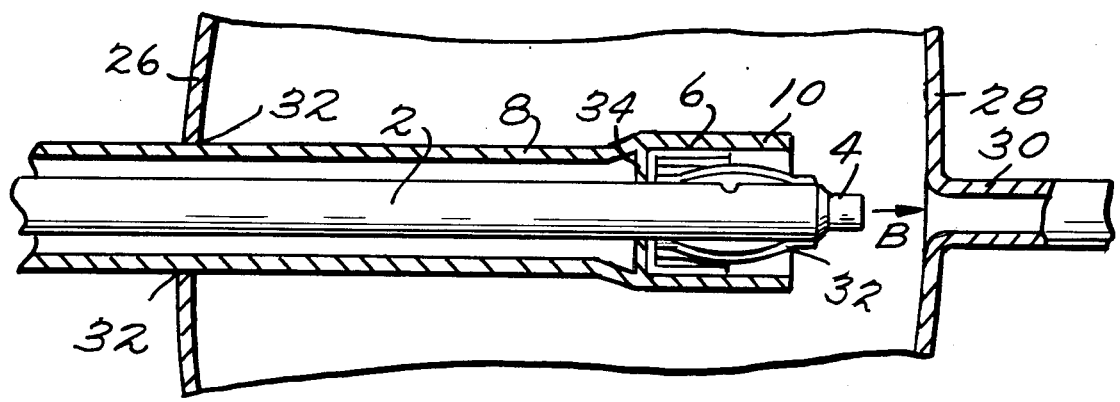
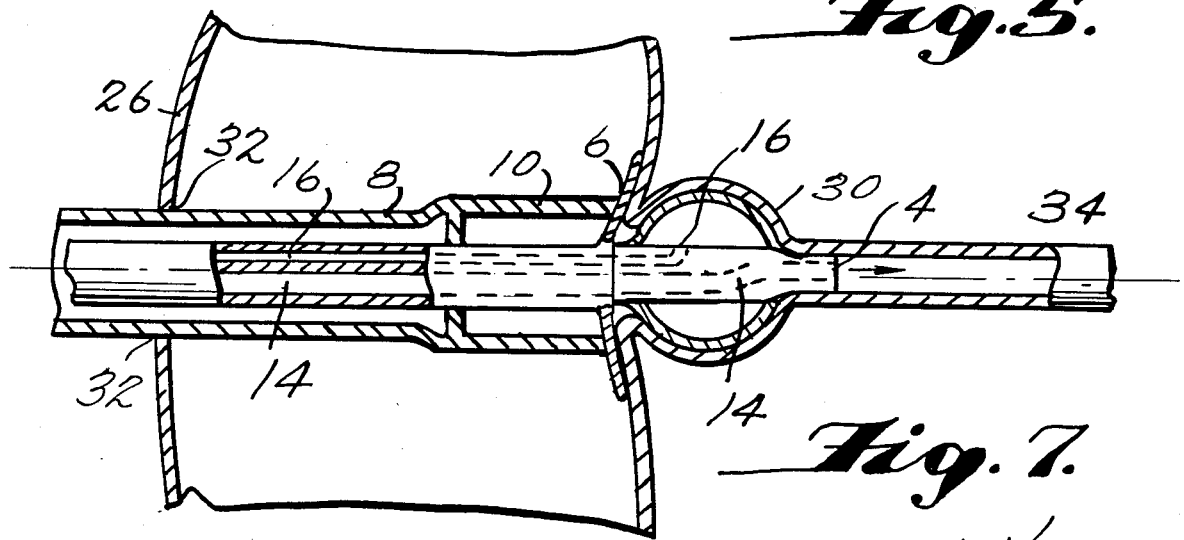
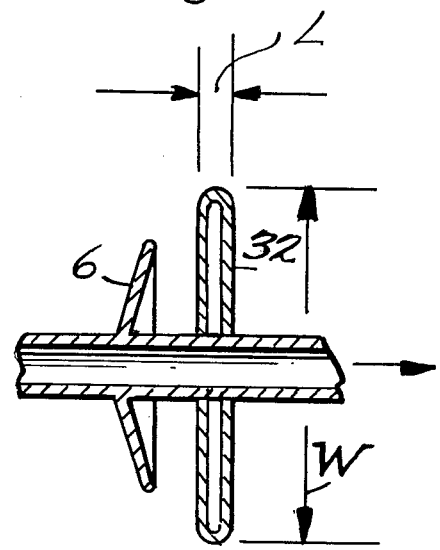
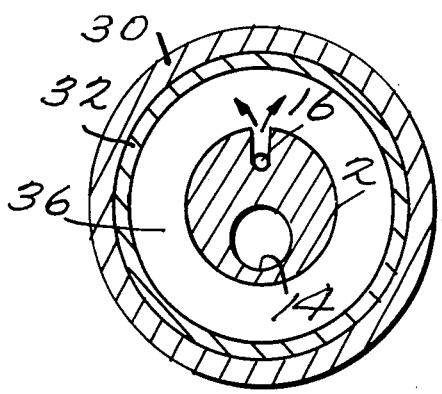

CATHETER HAVING MEANS FOR CONTROLLING THE INSERTION DEPTH

BACKGROUND OF THE INVENTION

The present invention relates to the field of catheters, and more particularly to a catheter having a flange to control the depth of insertion of the catheter.

Many catheters are known which are used to inject fluid to, or extract fluid from, an organ of a human being or similar animate object. One problem with such known catheters is that it is very difficult to control the insertion depth of the catheter into the organ. If the catheter is under-inserted, the fluid will not be provided to or extracted from the organ at the location desired. This can cause great difficulties when the catheter is used in surgery. The patient will not receive sufficient fluids from the catheter resulting in a failed operation. On the other hand, if the catheter is over-inserted the catheter may damage the organ walls in addition to providing fluid to or extracting fluid from the wrong location in the organ. Thus, it is necessary to insert a catheter to the correct depth within the organ. The present invention proposes a solution to this problem.

While the present invention is described in terms of a catheter to be used in retrograde cardioplegia solution administration in the coronary sinus during heart surgery, it is to be understood that the subject catheter may be used in any field of catheter application. Those having ordinary skill in this field will recognize the advantages of the claimed structure, and its application to a wide variety of catheter uses.

The problem of controlling the insertion depth of a catheter is particularly significant during open heart surgery. During such surgery, the patient's heart is stopped and the functions thereof are taken over by a heart-lung machine. In stopping the heart, care must be taken to prevent the heart muscle from continuing to beat without blood being supplied thereto. If the heart continues to beat without a proper blood supply, myocardial infarction (heart muscle necrosis) will result. In situations of ongoing ischemia, it is especially important to preserve mycardium.

To quickly and safely stop the patient's heart, it is known to provide a cardioplegia solution to the heart muscle which quickly arrests the muscle, thus preventing the heart from beating with an inadequate supply of blood. One way to provide such cardioplegia solution to the heart muscle is to inject it into the arteries leading to the heart muscle. Such antegrade introduction of the cardioplegia solution may be very difficult, however, due to aortic insufficiency or severe coronary arterial obstructions. Such insufficiency and obstructions prevent the adequate distribution of cardioplegia solution through the routine antegrade approach. Since many patients require heart surgery because of aortic insufficiency and/or severe coronary arterial obstruction, it is often difficult to provide the cardioplegia solution through the normal antegrade approach.

Another method of providing the cardioplegia solution to the heart muscle is called retrograde coronary sinus administration. In this approach, the cardioplegia solution is inserted into the veins leading from the heart muscle and then caused to flow backward (retrograde) into the heart muscle itself. Such a solution is attractive since the coronary veins of the heart muscle do not develop blockages. During retrograde coronary sinus cardioplegia solution administration, a catheter is inserted through the right atrium of the heart into the coronary sinus. Once in position, cardioplegia solution is caused to flow from the catheter into the coronary sinus, and from there back into the vein bed of the heart muscle itself. Such retrograde coronary sinus cardioplegia solution administration is a relatively new procedure with many advantages over the known antegrade approach.

A problem with the retrograde approach is the requirement to fully block the coronary sinus after the catheter has been inserted in order to prevent the cardioplegia solution from flowing backward from the coronary sinus into the right atrium. Another problem with the retrograde approach is controlling the insertion depth of the catheter into the coronary sinus. The right atrium and the coronary sinus are made of particularly fragile tissues which easily tear when probed with a catheter. If the catheter insertion depth is not properly controlled, extensive damage to the right atrium and/or the coronary sinus will result. Control of the insertion depth of the catheter is also important to provide the cardioplegia solution to the correct location in the coronary sinus and to prevent it from flowing back into the right atrium.

In France, retrograde coronary sinus administration of cardioplegia solution is being practiced but with a catheter that requires insertion under direct visual observation. Thus, the French approach is to cut open the right atrium and drain it, and then visually insert the catheter into the coronary sinus. Cutting open the right atrium requires a longer opertive time and adds to the risk of the surgery.

Thus, there is a need for a catheter whose insertion depth can be precisely controlled. For use in retrograde coronary sinus cardioplegia solution administration, such a catheter should include a device for blocking the coronary sinus to prevent the cardioplegia solution from flowing backward into the atrium. Such a catheter should also include a very soft tip to prevent tearing the walls of the right atrium and/or the coronary sinus. Such a catheter should also be capable of being inserted blindly without direct visualization so that it can be inserted through a purse string opening in the right atrium so that the right atrium does not have to be cut open.

SUMMARY OF THE INVENTION

The present invention provides a solution to the above-described problems. The present invention includes a catheter having a flange near the catheter end whereby the flange engages the wall of the right atrium while the tip of the catheter protrudes into the coronary sinus. The flange is located at a particular distance from the tip of the catheter to provide positive insertion depth control. Preferably, the flange is made of a soft plastic material which can assume an extended position substantially perpendicular to the tube length, and a collapsed position substantially parallel to the tube length. Thus, the catheter can be inserted through a purse string opening while the flange is in the collapsed position and then the flange can be opened to the extended position to engage the right atrial wall and precisely control the insertion depth of the catheter tip into the coronary sinus.

The catheter according to the present invention also includes an inflatable balloon positioned between the flange and the catheter tip. After insertion, the balloon is inflated to fully block the coronary sinus and prevent cardioplegia solution from flowing backward into the right atrium. The inflated balloon pinches vascular tissues between the flange and the balloon, thus insuring a very good seal. The catheter tube includes two passageways, a first passageway for the cardioplegia solution, and a second passageway for the inflating fluid which inflates the balloon.

Preferably, the catheter tip is made of a very soft plastic and is constructed so that the tip has a smaller wall thickness than the tube. Such a soft tip will prevent damage to the right atrium and/or coronary sinus walls.

The present invention also includes an introducer tube which surrounds the catheter tube and is axially movable with respect thereto. The introducer should include a receptacle at the end closest to the catheter tip. This receptacle is constructed to store the flange when it is in the collapsed position. The introducer is used to introduce the catheter tip through the purse string opening into the right atrium. Once inside the right atrium, the catheter tip is pushed further into the atrium while the introducer is held steady, thus causing the flange to move out of the receptacle to expand. As it expands, the flange assumes the extended position. The catheter tip is then inserted into the coronary sinus and the flange makes contacts with the right atrium wall, preventing further insertion of the catheter tip. When a positive coupling has been made between the flange and the atrium wall, the balloon is inflated, thus blocking the coronary sinus. At this point, the introducer may be pulled back and cardioplegia solution is injected through the catheter and caused to perfuse through the heart muscle vein bed.

Preferably, the inflatable balloon is constructed so that it inflates into an oblate, diaphragm-shape with a width greater than the length. Such a configuration provides more secure blockage of the coronary sinus.

BRIEF DESCRIPTION OF THE DRAWINGS

The structure and advantages of the subject invention will become more readily understood with reference to the following detailed description of the presently preferred exemplary embodiment when taken together with the attached drawings in which:

FIG. 4 is a cross-sectional view of the catheter after it has been inserted in the right atrium;

FIG. 5 is a cross-sectional view of the catheter after the catheter tip has been inserted into the coronary sinus;

FIG. 6 is a cross-sectional view of the catheter tip taken along line 6—6 of FIG. 5; and FIG. 7 is a cross-sectional view of the catheter tip showing a more oblate configuration of the balloon.

DETAILED DESCRIPTION OF THE PRESENTLY PREFERRED EXEMPLARY EMBODIMENT

The structure and advantages of the present invention will hereinafter be described with particular reference to a retrograde coronary sinus cardioplegia solution administration catheter. However, it is to be understood that the teachings of this invention are fully applicable to all cardiovascular catheters. Persons of ordinary skill in this field will readily understand that equivalent structures may be conceived which use the teachings of this invention. All such equivalent structures are to be included within the scope of this invention, which scope is as broad as the appended claims.

Figure 1:
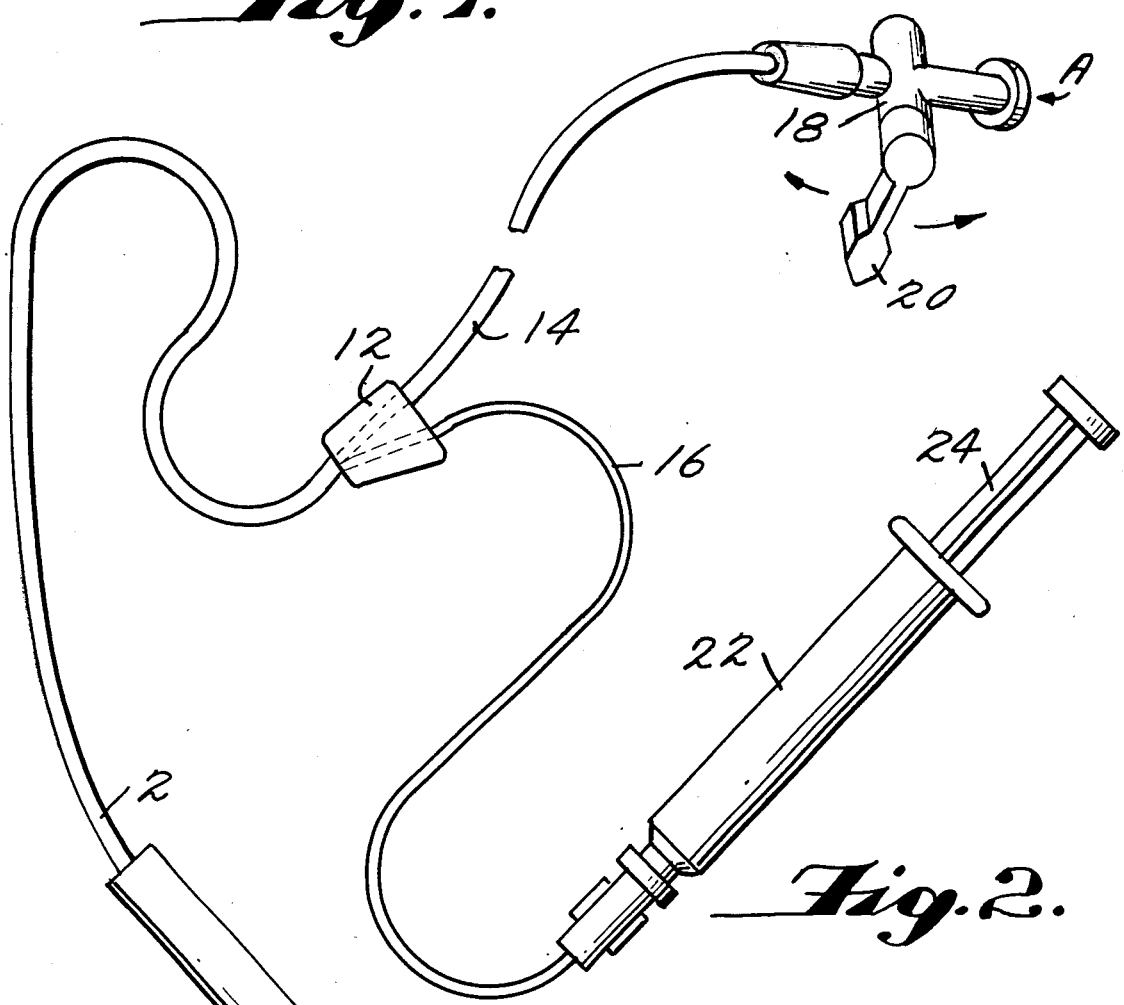
FIG. 1 is a plan view of the present invention, as embodied in a retrograde coronary sinus cardioplegia solution administration catheter.

FIG. 1 is a plan view of a retrograde coronary sinus cardioplegia solution administration catheter in accordance with the teachings of the present invention.

The retrograde coronary sinus cardioplegia solution administration catheter was designed to allow intraoperative placement through a purse string opening in the right atrium and permit easy and safe cannulation of the coronary sinus in order to continuously perfuse cardioplegia solution in a retrograde manner during cardiopulmonary bypass and global ichemic arrest of the heart. To insure safety during cannulation, a soft flexible catheter material is used with a disc flange near the tip to prevent over-insertion into and rupture of the coronary sinus. To facilitate guidance, a rigid or semi-rigid introducer is used to insert the catheter.

At the present time, no catheter is marketed in this country for use in the continuous administration of cardioplegia solution directly into the coronary sinus. Laboratory experiments using this technique have demonstrated excellent preservation of mycardium, especially in situations of ongoing ischemia such as an evolving mycardial infarction. It is a relatively new technique and the lack of a safe and easy-to-use catheter most likely explains the lack of clinical trials using this technique in this country. Retrograde coronary sinus administration of cardioplegia solution is being practiced in France using the earlier-described method. This method requires insertion of the catheter under direct visualization after opening the right atrium. The catheter described below obviates the need to open the right atrium as it can be inserted through a purse string opening, thus greatly simplifying the operative procedure and enhancing patient recovery. The present apparatus may offer distinct advantages in protecting the mycardium of patients who have aortic insufficiency or severe coronary arterial obstructions preventing adequate distribution of cardioplegia solution through the routine antegrade approach.

FIG. 1 depicts the retrograde coronary sinus cardioplegia solution administration catheter, as one embodiment of the present invention. The apparatus includes a catheter tube 2 having a catheter tip 4. Preferably, catheter tip 4 is made of a soft plastic material to prevent damage to the vessel walls of the patient. Preferably, the outside diameter of catheter tip 4 is less than that of the catheter tube 2. In addition, the wall thickness of catheter tip 4 should be less than the wall thickness of catheter tube 2. Such a catheter tip may be, for example, a Softip (trademark of Angiomedics Corp.).

Figure 3:
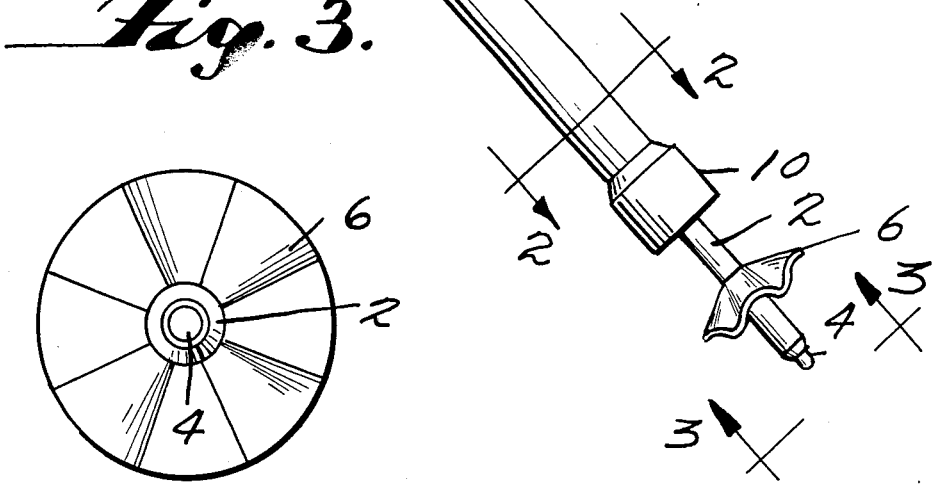
FIG. 3 is an end view of the catheter tip, as viewed from line 3—3 in FIG. 1.

A flange 6 is coupled to one end of the catheter tube 2 in the vicinity of catheter tip 4. Preferably, flange 6 is made of a soft, clear, resilient plastic material and has a substantially circular shape, although any convenient shape may be adopted depending on the catheter application. Thus, flange 6 presents a disc-like appearance, as depicted in FIG. 3. It is preferable that flange 6 is flexible so that it may assume an extended position at approximately a right angle to the catheter tube 2 (as depicted in FIGS. 1 and 5), and a collapsed position where flange 6 is substantially parallel to catheter tube 2 (as depicted in FIG. 4). Flange 6 is located at a predetermined distance from tip 4, to control the insertion depth. For the cardioplegia solution catheter, this distance may be 1-4 cm. Of course, this distance will vary in other catheter applications.

An introducer tube 8 surrounds catheter tube 2 and is substantially coaxial therewith. Introducer tube 8 is axially moveable with respect to catheter tube 2. Introducer tube 8 is preferably made of a semi-rigid, clear plastic having a smooth exterior surface to reduce friction when it is inserted through the purse string opening in the atrium. Receptacle 10 is located at the end of introducer tube 8 closest to catheter tip 4. Preferably, receptacle 10 is an enlarged section of introducer tube 8 having a larger outside diameter than the rest of the introducer tube. The operation of the introducer tube 8 and receptacle 10 will be more fully described in connection with FIGS. 4 and 5.

Catheter tube 2 has a junction block 12 at the proximal end thereof. As can be seen from FIG. 1, junction block 12 is used to guide solution tube 14 and air tube 16 into the catheter tube 2. As will be described in more detail later, both fluid tube 14 and air tube 16 run nearly the entire length of catheter tube 2 up to the vicinity of catheter tip 4. Fluid tube 14 is used to provide the cardioplegia solution from a solution storage device (not shown) to the distal end of the catheter tip 4. Those having ordinary skill in this field understand that fluid tube 14 may be used to inject any fluid into, or extract any fluid from the patient. As used in this specification and in the claims, the term "fluid" is used so as to encompass liquids, gases, air, etc.

Coupled to fluid tube 14 is fluid valve 18. Fluid valve 18 includes a lever 20 which is used to open and close fluid valve 18. The end of fluid valve 18 is adapted to be coupled to a fluid storage device which can provide fluid to valve 18 from the direction of arrow A. Manipulation of lever 20 causes fluid from the fluid storage receptacle to either flow through fluid valve 18 or to be blocked therein.

Air tube 16 is coupled to air syringe 22. Syringe 22 includes a handle 24 which, when pressed toward syringe 22, causes air to flow therefrom through air tube 16 along catheter tube 2. As will be described later, an inflatable balloon is coupled to the catheter distal end between flange 6 and catheter tip 4. Air syringe 22 and air tube 16 are adapted to provide inflating air to this balloon. Those having skill in this field will understand that any inflating medium such as gas, air, liquid, etc. may be used to adequately inflate the balloon. Furthermore, those having ordinary skill in this field will understand that other means of providing inflating fluid may be coupled to air tube 16. For example, an air pump, air bellows, pressurized gas, or a liquid pump may be used to introduce an inflating fluid through catheter tube 2 into the balloon.

Preferably, catheter tube 2, fluid tube 14, and air tube 16 are made of a flexible plastic material such as polyvinylchloride.

Figure 2:
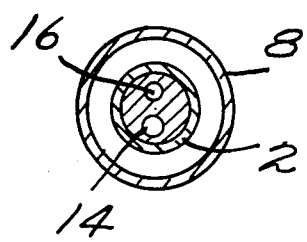
FIG. 2 is a cross-sectional view of the catheter taken along line 2—2 of FIG. 1.

FIG. 2 is a cross-sectional view of the apparatus taken along line 2—2 of FIG. 1. It can be seen that introducer tube 8 surrounds catheter tube 2 and is approximately coaxial therewith. A small space preferably exists between introducer tube 8 and catheter tube 2 so as to allow easy relative movement therebetween. Inside catheter tube 2 can be seen air tube 16 and fluid tube 14. While the drawing depicts air tube 16 being much smaller than fluid tube 14, it is to be understood that any sizes of tubes may be used which are most useful to the specific application for which the catheter is designed. As described above, fluid tube 14 is used to carry the fluid to or from the end of catheter tip 4. Air tube 16 is used to carry the inflating fluid from air syringe 22 to the balloon to be described later.

FIG. 3 is an end view of the catheter, as viewed from line 3—3 of FIG. 1. FIG. 3 shows that flange 6 is disc-shaped and has catheter tube 2 extending therethrough at substantially the center of the disc. It can be seen that catheter tip 4 has a smaller outside diameter and a smaller wall thickness than catheter tube 2. As shown in FIGS. 1 and 3, flange 6 is made of a soft, flexible plastic material which is capable of being collapsed and opened, much like an umbrella. In the extended position, flange 6 forms an obtuse angle (substantially perpendicular) with catheter tube 2. In the collapsed position (see FIG. 4), flange 6 is folded to be substantially parallel to catheter tube 2. Preferably, flange 6 is made of a soft, clear plastic material such as polyvinylchloride. The outside diameter of flange 6 is approximately 2 cm for this application. Those who are skilled in this field will understand that various sizes of flanges may be provided depending upon the use for which the catheter is designed.

FIGS. 4 and 5 are cross-sectional diagrams showing the present invention inserted in the heart of a patient. FIG. 4 shows the apparatus inserted into the patient's right atrium while FIG. 5 shows the catheter inserted into the coronary sinus. The right atrium includes a front wall 26 and a rear wall 28. Extending from rear wall 28 is the coronary sinus 30.

In order to install the catheter into the atrium, a purse string opening 32 is formed in atrium wall 26. Purse string opening 32 is made only large enough to accommodate the outside diameters of introducer tube 8 and receptacle 10.

The catheter is then inserted into the atrium through purse string opening 32. When it is so inserted, catheter tube 2, flange 6, and introducer tube 8 are in the configuration shown in FIG. 4. In this configuration, introducer tube 8 has been pushed as far toward catheter tip 4 as possible. This causes flange 6 to be collapsed within receptacle 10 so that the flange is substantially parallel to catheter tube 2, as shown in FIG. 4. Preferably, introducer tube 8 includes annular flange 34 which contacts the base of flange 6 to arrest the movement of introducer tube 8 along catheter tube 2 in the direction of catheter tip 4, and to prevent the flow of air or fluid in the space between tube 2 and introducer 8.

After the apparatus has been inserted into the atrium through purse string opening 32, introducer tube 8 is held steady while catheter tube 2 is pushed in the direction of Arrow B. In this case, catheter tip 4 is pushed toward coronary sinus 30. Since catheter tip 4 is made of a very soft and flexible plastic material, tip 4 can be inserted into coronary sinus 30 without unnecessarily rupturing or tearing the walls of coronary sinus 30 or atrial wall 28.

As catheter tube 2 exits from introducer tube 8, flange 6 expands to resume its original disc-shaped configuration. Once the flange is in its fully extended position, catheter tube 2 is inserted further into coronary sinus 30. When flange 6 abuts atrial wall 28, catheter tube 2 can proceed no further into coronary sinus 30, thus controlling the insertion depth of the catheter into the coronary sinus. This is depicted in FIG. 5. Once flange 6 abuts atrial wall 28, it is preferable to push introducer tube 8 in the direction of Arrow B in order to firmly lock flange 6 to atrium wall 28. This is also depicted in FIG. 5. Thus, the above-described apparatus provides an accurate depth-insertion control for catheter tube 2. Flange 6 may be placed at any appropriate location on catheter tube 2, depending upon the insertion depth required for the particular application.

Once catheter tip 4 and the end of catheter tube 2 are inserted into coronary sinus 30, it is preferable (at least in the cardioplegia solution administration embodiment) to block the coronary sinus 30 to prevent the cardioplegia solution from flowing backward from coronary sinus 30 into the atrium and to prevent inadvertent removal of the catheter from the sinus. For this, an inflatable balloon 32 is provided on the catheter tube 2 substantially between flange 6 and catheter tip 4. Preferably, inflatable balloon 32 is made of a translucent plastic material which is integrally connected with catheter tube 2 in an air-tight manner. The end of air tube 16 is designed to supply inflating fluid to the inside of balloon 32, as depicted in FIG. 5. Thus, by manipulating handle 24 and air syringe 22, inflating fluid is caused to flow through air tube 16 and into inflatable balloon 32, thus inflating the balloon. As the balloon is inflated, it abuts the wall of coronary sinus 30, thus blocking fluid flow between coronary sinus 30 and the atrium, and anchoring the catheter in the sinus.

Once the catheter tip is firmly inserted into the coronary sinus and inflatable balloon 32 is inflated, the cardioplegia solution is introduced into the coronary sinus through fluid tube 14, in the direction of Arrow C. Now, cardioplegia solution enters coronary sinus 30 and perfuses, in a retrograde manner, through the venous bed of the heart muscle. Inflatable balloon 32 prevents the cardioplegia solution from flowing backward into the atrium. Flange 6 prevents the catheter from being over inserted into the coronary sinus and acts as a further fluid-tight seal between the coronary sinus and the atrium. In such a fashion, cardioplegia solution can be reliably provided to the coronary sinus 30 without direct visualization of the coronary sinus or of the catheter tip. Thus, cardioplegia solution may be reliably provided to the coronary sinus of the patient without unnecessary opening of the atrium. Such apparatus further provides insertion depth control and allows the catheter to be inserted with minimal damage to the walls of the atrium and the coronary sinus.

The location of inflatable balloon 32 with respect to catheter tip 4 and flange 6 may vary depending upon the catheter application. However, for cardioplegia solution administration applications, it is preferable that the end of balloon 32 is approximately 2–4 mm from the base of flange 6. This provides the best configuration of flange and balloon whereby the opening between atrium wall 28 and coronary sinus 30 is "pinched" thus providing a good fluid-tight seal. Furthermore, it is preferable that the other end of inflatable balloon 32 is approximately 5–10 mm from catheter tip 4. This allows for proper positioning of the catheter tip within the walls of coronary sinus 30.

In FIG. 5, it can be seen that the catheter tube longitudinal axis 34 forms an obtuse angle with flange 6. While this angle is approximately 80° in FIG. 5, those having skill in this field will understand that any appropriate obtuse angle may be chosen, depending upon the catheter application. In fact, situations can be perceived where the angle between flange 6 and longitudinal axis 34 would be an acute angle. Nevertheless, flange 6 still operates to control the insertion depth of the catheter tube 2. In FIGS. 4 and 5, the opening between atrial wall 28 and coronary sinus 30 may be termed as the catheter application location. Those having skill in this field will understand that catheter application locations may vary in configuration and size depending upon the particular application for which the catheter is designed. The scope of the present invention is intended to include all such catheter configurations and applications requiring control of the insertion depth.

FIG. 6 is a cross-sectional view of inflatable balloon 32, taken along line 6—6 of FIG. 5. In its inflated condition, inflatable balloon 32 abuts the wall of coronary sinus 30 in a fluid-tight (or substantially fluid-tight) manner. In this inflated condition, an air gap 36 exists between catheter tube 2 and the skin of inflatable balloon 32. Air (or any other inflating fluid) is supplied to air gap 36 through air tube 16. Arrows D indicate the direction of air flow from air tube 16 into air gap 36. Fluid tube 14 is adapted to carry the cardioplegia solution through catheter tip 4 into coronary sinus 30. FIG. 6 shows that inflatable balloon 32 uniformly surrounds catheter tube 2 and is substantially coaxial therewith. Those having skill in this field will understand that inflatable balloon 32 may be coupled to catheter tube 2 in any configuration (for example eccentric, etc) depending upon the desired application.

FIG. 7 depicts a preferred embodiment of inflatable balloon 32. In this embodiment, the balloon presents a more oblate, diaphragm-like configuration. As can be seen in FIG. 7, the diaphragm width W (extending perpendicular to longitudinal lock axis 34) is greater than the balloon length L (extending substantially parallel to longitudinal axis 34). In fact, it is preferred that width W is much greater than length L so that inflatable balloon 32 presents a diaphragm-like appearance. With such a configuration, obstruction of the coronary sinus is minimized while a fluid tight seal is achieved. In addition, the opening between atrium wall 28 and coronary sinus 30 is more substantially pinched between flange 6 and balloon 32, thus creating an even more fluid-tight seal.

Thus, what has been described is a catheter having insertion control means which is particularly adapted to an application in retrograde coronary sinus cardioplegia solution administration. Again, those having ordinary skill in this field will understand that the teachings of this invention may be applied in a wide variety of catheter applications. Thus, while the invention has been described in connection with what is presently considered to be the most practical and preferred embodiment, it is to be understood that the invention is not limited to the disclosed embodiment. On the contrary, the teachings of this invention are intended to cover various modifications and equivalent arrangements included within the spirit and scope and of the appended claims. This scope is to be accorded the broadest interpretation so as to encompass all such equivalent modifications and structures.

I claim:

1. Cardiovascular catheter apparatus of a size for introduction into a cardiovasuclar system, comprising:
    tube means having distal and proximal ends and a longitudinal axis, adapted for passing a fluid to or from a cardiovascular structure;
    said tube means including a flexible, resilient deformable and radially extending depth control flange means, coupled to said tube means near said distal end, for controlling an insertion depth of said tube distal end into said cardiovascular structure, said flange means being constructed such that it is movable from a collapsed to an extended position thereby forming an obtuse angle with respect to said tube means; and inflatable means, coupled to said tube means between said flange means and said distal end at a distance from said flange means to pinch vascular tissue, which tissue surrounds an opening, between said flange means and said inflatable means.

2. Apparatus according to claim 1 wherein said flange means comprises a plastic disc which is movable between an extended position where it extends radially from said tube means whereby it forms said obtuse angle with said tube, and a collapsed position where said flange means is substantially collapsed on said tube means, and further including tubular introducer means, coaxially surrounding and axially movable with respect to said tube means and having an insertion end storing the collapsed flange means, for introducing said tube means distal end into said cardiovascular structure.

3. Apparatus according to claim 1 wherein said inflatable means comprises a plastic balloon having a length extending in a lengthwise direction of said tube means, and a width extending substantially perpendicular to said tube lengthwise direction, and wherein said plastic balloon width is greater than said plastic balloon length when said plastic balloon is substantially fully inflated.

4. Apparatus according to claim 1 wherein said tube means distal end includes a soft, flexible tip having an outside diameter that is less than an outside diameter of said tube means.

5. A catheter according to claim 1 wherein said tube includes first and second fluid carrying channels, said first channel being adapted to carry an inflating fluid to said inflatable means, said second channel being adapted to carry a fluid between said tube distal end and the tube proximal end.

6. A catheter according to claim 5 further including:
inflating fluid supply means adapted for supplying inflating fluid to said first channel; and
valve means, coupled to said second fluid carrying channel, for controlling a supply of fluid to said second channel.

7. A catheter according to claim 1 wherein said flange includes a flexible plastic disc having a center portion through which passes said catheter tube.

8. A catheter according to claim 1 wherein said catheter tube distal end includes a flexible tip which has an outside diameter that is less than an outside diameter of said catheter tube.

9. A catheter according to claim 1 wherein said inflatable means has a length extending in a lengthwise direction of said tube, and a width extending substantially perpendicular to said tube lengthwise direction, and wherein said inflatable means width is greater than said inflatable means length when said inflatable means is substantially fully inflated.

10. Cardiovascular catheter apparatus of a size for introduction into a cardiovascular system, comprising:
tube means having distal and proximal ends and a longitudinal axis, adapted for passing a fluid to or from a cardiovascular structure;
said tube including a flexible, resilient depth control flange means, coupled to said tube means near said distal end, for controlling an insertion depth of said tube distal end into said cardiovascular structure, said flange being movable between an extended position where it extends radially from said tube means whereby it forms an obtuse angle with respect to said tube means, and a collapsed position where it is substantially collapsed on said tube means;
tubular introducer means, coaxially surrounding and axially movable with respect to said tube means and having an insertion end storing the collapsed flange means, for introducing said tube means distal end into said cardiovascular structure; and
inflatable means, coupled to said tube means between said flange means and said distal end at a distance from said flange means to pinch vascular tissue, which tissue surrounds an opening, between said flange means and said inflatable means.

11. A catheter according to claim 10 wherein said flange is substantially circular in shape and is made of a flexible plastic material.

12. A catheter according to claim 10 wherein said introducer means includes a receptacle at said insertion end for storing said flange when said flange is in said collapsed position.

13. A catheter according to claim 10 further including first and second fluid carrying means, disposed in said tube means, for carrying fluid, said first fluid carrying means being coupled to said inflatable means and adapted for supplying inflating fluid to said inflatable means, said second fluid carrying means adapted for supplying a fluid to said tube means distal end.

14. A method of inserting a cardiovascular catheter into a cardiovascular structure, comprising the steps of:
inserting a catheter tube distal end into an opening in said cardiovasular structure;
controlling an insertion depth of said tube distal end by abutting a flexible resilient flange, which flange is fixed to said catheter tube near said distal end, against vascular tissue surrounding said opening; and
sealing said catheter tube distal end in said opening by inflating an inflatable balloon, said balloon coupled to said tube between said distal end and said flange at a predetermined distance from said flange, to cause said vascular tissues surrounding said opening to be pinched between the inflated balloon and said flange.

15. A method according to claim 14 further including the steps of:
surrounding said tube with a tubular introducer which is substantially coaxial with and axially movable with respect to said tube, said introducer having a receptacle in a distal end thereof; and
moving said flange between a collapsed position where it is substantially collapsed on said tube and stored inside said introducer receptacle, and an extended position where said flange extends radially from said tube and forms an obtuse angle therewith.

16. A method according to claim 15 further including the step of axially moving said introducer in a direction away from said tube distal end to cause said flange to move from said collapsed position to said extended position.

17. A method according to claim 16 wherein said sealing step comprises the step of inflating an inflatable balloon which has a greater width than depth, said width being a direction substantially perpendicular to said tube, said depth being substantially parallel to said tube.

* * * * *